United States Patent
Foster et al.

(10) Patent No.: US 9,694,172 B2
(45) Date of Patent: Jul. 4, 2017

(54) IMPLANTABLE MEDICAL DEVICES WITH SEPARATE FIXATION MECHANISM

(71) Applicant: Cardiac Pacemakers, Inc., St. Paul, MN (US)

(72) Inventors: Arthur J. Foster, Blaine, MN (US); Bruce Alan Tockman, Scandia, MN (US); Lili Liu, Maple Grove, MN (US); Howard D. Simms, Jr., Shoreview, MN (US); Anne-Marie Bustillos, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 424 days.

(21) Appl. No.: 14/207,112

(22) Filed: Mar. 12, 2014

(65) Prior Publication Data

US 2014/0276929 A1    Sep. 18, 2014

Related U.S. Application Data

(60) Provisional application No. 61/777,056, filed on Mar. 12, 2013.

(51) Int. Cl.
*A61N 1/05* (2006.01)

(52) U.S. Cl.
CPC .............. *A61N 1/05* (2013.01); *A61N 1/059* (2013.01); *A61N 1/0573* (2013.01); *A61N 1/0595* (2013.01)

(58) Field of Classification Search
CPC .................... A61N 1/0587; A61B 2018/00363
See application file for complete search history.

(56) References Cited

U.S. PATENT DOCUMENTS 5,154,183 A * 10/1992 Kreyenhagen ....... A61N 1/0587
                                                            600/375
7,212,871 B1    5/2007 Morgan
(Continued)

FOREIGN PATENT DOCUMENTS

WO    2012051235 A1    4/2012

OTHER PUBLICATIONS

Notification of Transmittal of the International Search Report and the Written Opinion of the International Searching Authority, or the Declaration, Jun. 18, 2014, 14 pages.

*Primary Examiner* — Edward Moran
*Assistant Examiner* — Natasha Patel
(74) *Attorney, Agent, or Firm* — Seager, Tufte & Wickhem LLP

(57) ABSTRACT

Devices or methods such as for stimulating excitable tissue or sensing physiologic response or other signals that can use separate fixation mechanism is described. An implantable apparatus can include a modular electrostimulation electrode assembly that can include a first module and a second module that can be end user-attachable to each other and end user-detached from each other. The first module can include an electrostimulation electrode fixation support member that can be laid flat against or otherwise conform to a surface of a heart, and can define a centrally located open portal such as for permitting electrode access to the surface of the heart. The second module can include an electrostimulation electrode that can be inserted through the portal of the fixation support member such as to contact the surface of the heart such as to deliver chronic electrostimulation to the heart.

15 Claims, 9 Drawing Sheets

(56) References Cited

U.S. PATENT DOCUMENTS

| | | | |
|---|---|---|---|
| 7,319,905 B1 | 1/2008 | Morgan et al. | |
| 7,418,298 B2 | 8/2008 | Shiroff et al. | |
| 7,433,739 B1 | 10/2008 | Salys et al. | |
| 7,496,410 B2 | 2/2009 | Heil, Jr. | |
| 7,546,166 B2 | 6/2009 | Michels et al. | |
| 7,657,326 B2 | 2/2010 | Bodner et al. | |
| 7,711,437 B1 | 5/2010 | Bornzin et al. | |
| 7,751,905 B2 | 7/2010 | Feldmann et al. | |
| 7,783,366 B1 * | 8/2010 | Morgan | A61N 1/0587 607/129 |
| 7,848,821 B1 * | 12/2010 | Ryu | A61N 1/0573 607/122 |
| 7,860,581 B2 | 12/2010 | Eckerdal et al. | |
| 7,899,550 B1 | 3/2011 | Doan et al. | |
| 7,920,927 B2 | 4/2011 | Zarembo | |
| 7,920,928 B1 | 4/2011 | Yang et al. | |
| 8,000,805 B2 | 8/2011 | Swoyer et al. | |
| 8,036,756 B2 | 10/2011 | Swoyer et al. | |
| 8,036,757 B2 | 10/2011 | Worley | |
| 8,086,324 B1 * | 12/2011 | Vase | A61N 1/0587 607/125 |
| 8,090,451 B2 | 1/2012 | Tyson, Jr. | |
| 8,565,897 B2 | 10/2013 | Regnier et al. | |
| 9,037,262 B2 | 5/2015 | Regnier et al. | |
| 2007/0106336 A1 * | 5/2007 | Schaer | A61F 2/2481 607/37 |
| 2007/0293904 A1 | 12/2007 | Gelbart et al. | |
| 2009/0204170 A1 | 8/2009 | Hastings et al. | |
| 2012/0330392 A1 | 12/2012 | Regnier et al. | |
| 2013/0053921 A1 | 2/2013 | Bonner et al. | |
| 2014/0046395 A1 | 2/2014 | Regnier et al. | |
| 2015/0374976 A1 | 12/2015 | Regnier et al. | |

\* cited by examiner

IMPLANTABLE MEDICAL DEVICES WITH SEPARATE FIXATION MECHANISM

CLAIM OF PRIORITY

This application claims the benefit of priority under 35 U.S.C. §119(e) of U.S. Provisional Patent Application Ser. No. 61/777,056, filed on Mar. 12, 2013, which is herein incorporated by reference in its entirety.

TECHNICAL FIELD

This document relates generally to medical devices, and more particularly, to devices and methods for stimulating excitable tissue or sensing physiologic response.

BACKGROUND

Ambulatory medical devices, such as implantable pacemakers and cardioverter-defibrillators, can chronically stimulate excitable tissues or organs, such as a heart, such as to treat abnormal cardiac rhythms such as bradycardia or tachycardia, or to help improve cardiac performance such as by correcting cardiac dyssynchrony in a patient with congestive heart failure (CHF). Such ambulatory medical devices can have one or more electrodes that can be positioned within the heart or on a surface of the heart for contacting the cardiac tissue. The electrodes can be electrically coupled to an electronics unit such as a pulse generator, such as via a lead, and can be used to deliver one or more electrostimulations to the heart, such as to restore the normal heart function.

OVERVIEW

Cardiac stimulation using an implantable medical device can involve one or more leads that can be transvascularly inserted into one of the heart chambers, such as an atrium or a ventricle. Stimulation of the heart can be accomplished through direct myocardium stimulation, such as from one or more electrodes that can be affixed to the cardiac tissue, at specified stimulation strength (e.g., stimulation energy) that can be sufficient to capture the heart, resulting in an evoked electrical depolarization and mechanical contraction. The minimum of amount of energy needed to reliably and consistently cause the capture can be referred to as a capture threshold. The capture threshold can be affected by one or more factors such as the conductivity of the myocardium at the stimulation site, healing of the traumatized tissue, patient disease progression, or medication. For example, electrode assembly fixation to the heart tissue can cause tissue trauma at the fixation site. Because the electrode is typically placed in close proximity to the electrode assembly fixation site, the capture threshold can become elevated (e.g., as a result of fibrous tissue growth) such that the device output energy can be insufficient to capture the myocardium and achieve desired therapeutic effect. An inconsistent capture threshold can also preclude receiving effective stimulation therapy, or can increase the device output energy needed, such as to compensate for the elevated capture threshold. This can increase battery power consumption and can thereby reduce the device longevity. Additionally, the lead and electrodes may require replacement such as due to lead fracture or malfunction. Removal of electrodes encapsulated by fibrosis can involve trauma to a patient.

Some patients, such as children or persons with a compromised venous system, can benefit from epicardial electrostimulation, such as using one or more electrodes (with or without a lead) that can be affixed on the heart surface for stimulation. Epicardial stimulation of the heart can face the challenge of uncertainty in proper lead and electrode placement. For example, epicardial stimulation can be associated with a higher capture threshold than endocardial stimulation, such as due to higher energy demand for capturing the myocardium from the heart's outer surface. The present inventors have recognized that it can be desirable to locate an epicardial site with a lower capture threshold such as to conserve energy stored or used by the device. Also, there are tissues on the heart surface that can be more prone to trauma or severance damage, such as coronary arteries or nerve tissues. In some implantation procedures, these vulnerable tissues may be avoided when positioning or affixing the lead or electrodes to the epicardial surface of the heart. Thus, the present inventors have recognized that there remains a considerable need for better devices and methods, such as for improving the reliability and consistency of chronic cardiac stimulation and reducing the trauma associated with electrode or lead removal.

Various embodiments described herein can help improve electrical cardiac stimulation or can reduce trauma such as can be associated with stimulation electrode or lead replacement. For example, an implantable apparatus can comprise a modular electrostimulation electrode assembly. A first module can include an electrostimulation electrode fixation support member, which can be laid flat against or otherwise conform to a surface of a heart of a subject, and can be affixed to a desired site of the heart. The fixation support member can define a centrally located open portal, such as can permit electrode access to the surface of the heart therethrough. A second module can include an electrostimulation electrode that can be inserted through the centrally located open portal of the fixation support member to contact the surface of the heart. The second module can be coupled to an electrostimulation system via a wired or wireless connection including, for example, a leadwire, and deliver chronic electrostimulation to the heart. The second module can include an untethered medical device such as a self-contained electrostimulator device. The first and second modules can have respective coupler features, such as can allow the two modules to be end user-attached securely to each other and end user-detached from each other.

A method example can include attaching a first module, which can include a fixation support member, to a temporary third module that can include an electrostimulation electrode. When the first and third modules are attached, the electrostimulation electrode can be located within a portal of the fixation support member. The attached first and third modules can be positioned at a position at the heart where the electrostimulation threshold can be tested. In response to a detection of a desired value of the electrostimulation threshold, the first module can be affixed at the corresponding position at the heart, and the third module can then be detached from the first module. A second module can then be affixed to the first module. The second module can includes one or more electrostimulation electrode that can deliver chronic electrostimulation to the heart at the position at the heart.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are apparatuses and methods for stimulating a target site of a heart in a patient, such as to achieve desired a diagnostic or therapeutic effect. The target site can include an epicardial or endocardial site. The stimulation apparatus can be modularized such that a module including one or more electrostimulation electrodes can be attachable to and detachable from another module that can include a fixation support member. The apparatus and the methods described herein can also be applicable to stimulation or sensing of other tissues or organs in the body.

Figure 1:
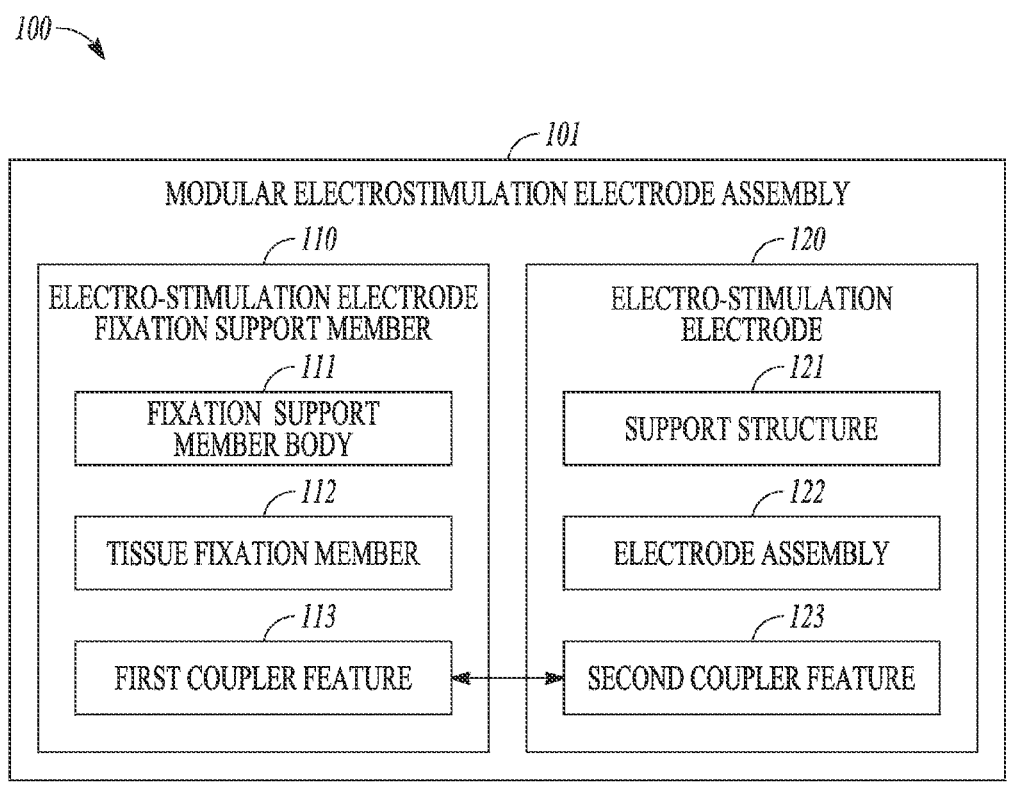
FIG. 1 illustrates an example of an implantable apparatus comprising a modular electrostimulation electrode assembly.

FIG. 1 illustrates a schematic example of an implantable apparatus 100 that can include a modular electrostimulation electrode assembly 101. The modular electrostimulation electrode assembly 101 can be configured to be affixed to an endocardial or epicardial location or region of the heart such as to provide chronic stimulation to the heart. For example, the modular electrostimulation electrode assembly 101 can be chronically affixed to a surface of the heart, and can be configured to sense a biopotential from the heart or to deliver an electrostimulation to the surface of the heart. At least a portion of the modular electrostimulation electrode assembly 101 can be configured to be affixed to a site of other tissue or another organ such as to stimulate the tissue or organ. Examples of such organs or tissues can include an interior or exterior of an artery or vein, a nerve bundle, skin, a carotid body, a stomach or intestine, a bladder, a kidney, soft tissue, gastric tissue, or neural tissue.

The modular electrostimulation electrode assembly 101 can include a first module, which can include an electrostimulation electrode fixation support member 110, and a second module which can include an electrostimulation electrode 120. The electrode fixation support member 110 and the electrostimulation electrode 120 can be configured to be engaged with each other or disengaged from each other, such as by an end-user.

The electrostimulation electrode fixation support member 110 can be configured to be chronically placed at and in close contact with a target site of the tissue or organ to be stimulated, such as the endocardial or epicardial heart surface. The electrode fixation support member 110 can include a fixation support member body 111, a tissue fixation member 112, and a first coupler feature 113. The fixation support member body 111 can be made out of one or materials that can include stainless steel, titanium alloy, a polymer, or one or more other synthetic biocompatible materials. To encourage close contact between the electrode fixation support member 110 and the target tissue, the fixation support member body 11 can have at least one flat or conformal tissue-contact surface. In an example, the fixation support member body 111 can be sized, shaped, or otherwise configured to lay flat against or otherwise conform to a surface of the heart, such as against a portion of the epicardium. In an example, the tissue-contact surface of the electrode fixation support member 110 can have a concave, convex, or other curved shape that can match, approximate, or conform to the contour of the target site of stimulation. The electrode fixation support member 110, or a portion thereof, can have a disk-like shape. In an example, the width of the electrode fixation support member 110 can be greater than the height of the electrode fixation support member 110. As an example, the tissue-contacting surface can have a diameter of approximately 6-25 millimeters, and a surface area of approximately 30-500 square millimeters.

In an example, the fixation support member body 111 can include an open portal that can be sized, shaped, or otherwise configured to be capable of permitting electrode access through the portal to the tissue surface of the heart. The open portal can be configured to help enable the end user to visualize the location where the tissue fixation member 112 or other parts of the electrode fixation support member 110 is positioned to interface with the target tissue. For example, the fixation support member body 111 can include a viewable zone that can allow or facilitate an end user (e.g., a surgeon) to avoid placing or fixing the electrode fixation support member 110 at a location at which the tissue is more prone to trauma or severance damage, such as at a location of an artery, a nerve, or other sensitive tissue. This can potentially help eliminate or reduce the exposure of diagnostic radiation such as fluoroscopy. In an example, the open portal can be located at or near the center of the fixation support member body 111. For example, the fixation support member body 111 can include a ring shape such that the center portion of the fixation support member body 111 can provide an open portal that can provide an unobstructed view of the site of fixation.

The tissue fixation member 112 can be located on the tissue-contacting surface of the fixation support member body 111. The tissue fixation member 112 can be sized, shaped, or otherwise configured to allow the electrode fixation support member 110 to be chronically and securely affixed to the target tissue such as the heart surface. The tissue fixation member 112 can include a passive fixation mechanism, an active fixation mechanism, a combination of one or more passive or active fixation mechanisms, or biocompatible glue. Examples of the passive fixation can include one or more tines, one or more fins, one or more helices, or one or more other extension structures. Examples of the active fixation can include one or more screws, one or more hooks, one or more barbs, one or more helices, or one or more other tissue-penetrating mechanisms. The tissue fixation member 112 can be such oriented that the tissue fixation member 112 need not block all or a portion of the viewable zone of the open portal.

In an example, the tissue fixation member 112 can include a suture retention feature. For example, the suture retention feature can be located at one or more sites on the fixation support member body 111 or at a dedicated or other suture area that can be attached to the fixation support member body 111. The suture retention feature can allow for or facilitate suturing the electrode fixation support member 110 to the target tissue. For example, at least a portion of the electrode fixation support member 110 can include a port, a receptacle, a bridge, a loop, or a fabric that can be configured to permit suturing therethrough.

In an example, at least a portion of the electrode fixation support member 110 can be textured or porous, such as on a scale that can be configured to permit or facilitate tissue ingrowth. For example, the fibrotic tissue that can be formed around the tissue fixation member 112 can at least help more firmly hold the electrode fixation support member 110 against the target tissue. In an example, the tissue fixation member 112 can include porous biomaterial or porous synthesized material, which can be attached to or covered on at least a portion of the fixation support member body 111 (such as at the tissue-contacting surface), such as to allow or promote tissue ingrowth. Examples of the porous material can include one or more of: titanium or stainless steel fiber mesh, porous tantalum, or polyester or heavyweight polypropylene mesh, among others.

The first coupler feature 113 can be configured to be coupled to the electrostimulation electrode 120 such as via a second coupler feature 123 that can be provided on or within the electro-stimulation electrode 120. In an example, the first coupler feature 113 and the second coupler feature 123 can be sized, shaped, or otherwise configured to be attached securely to each other, such as by an end user, such as to attach the first module of electrode fixation support member 110 and the second module of electro-stimulation electrode 120. The first coupler feature 113 and the second coupler feature 123 can also be detached from each other, such as by an end user, such as to detach the first module of the electrode fixation support member 110 and the second module of electro-stimulation electrode 120 from each other. Examples of the first coupler feature 113 and the second coupler feature 123 can include a snap-fit coupling, a threaded or other rotation or screw-in coupling, a slide-in engagement, or one or more other locking mechanisms.

The electrostimulation electrode 120 can be sized, shaped, or otherwise configured to be inserted through the portal on the fixation support member body 111 such as to contact the target tissue, such as the heart surface. In an example, the electrostimulation electrode 120 can be a part of a stimulation delivery system. The electrostimulation electrode 120 can include one more individually addressable electrodes, which can be individually electrically connected to a stimulator, such as via separate conductors that can be mutually insulated from each other and that can be encapsulated, such as in a lead or catheter. The stimulator, such as an ambulatory medical device or an external pacing system analyzer (PSA) circuit, can be separate from and external to the modular electrostimulation electrode assembly 101. In an example, the electrostimulation electrode 120 can include an untethered electrostimulator device such as an implantable electrostimulator, which need not be tethered to another device by a leadwire or other wired connection. Examples of the untethered electrostimulator device are discussed below, such as with reference to FIGS. 4A-B.

As illustrated in FIG. 1, the electrostimulation electrode 120 can include a support structure 121, an electrode assembly 122, and a second coupler feature 123. The support structure 121 can be shaped or sized or otherwise configured to hold the electrode assembly 122 in place such that the electrode assembly 122 can be positioned to the desired location on the target tissue. The support structure 121 can have a comparable shape as the fixation support member body 111. For example, both the fixation support member body 111 and the support structure 121 can have disk-like shapes. When the electrostimulation electrode 120 constitutes an untethered electrostimulator device, the support structure 121 can be configured to carry or house the electrostimulation generation circuitry or one or more other electrical components of the stimulator. The support structure 121 can serve as the housing or "can" of the ambulatory medical device.

The electrode assembly 122 can be configured to contact the target tissue and to deliver the electrostimulation thereto or therein. The electrode assembly 122 can include one or more individually addressable electrodes. In an example, the electrode assembly 122 can include an electrode array that can include two or more electrodes. The electrode array can include electrodes that can be spatially distributed, such as according to a specified shape or orientation, such as in a linear array, a planar array, or a three-dimensional array. The electrode assembly 122, which can be held and secured by the support structure 121, can be sized, shaped, or otherwise configured to access the target tissue through the open portal of the electrode fixation support member 110 when the electrode fixation support member 110 and the electrostimulation electrode 120 are attached to each other, such as through their respective coupler features.

The second coupler feature 123 can be sized, shaped, or otherwise configured to be physically coupled to the first coupler feature 113, such as for causing the first module of electrode fixation support member 110 and the second module of electro-stimulation electrode 120 to securely attach to each other. The second coupler feature 123 can also be de-coupled from the first coupler feature 113, such as for causing the first module of the electrode fixation support member 110 and the second module of the electro-stimulation electrode 120 to detach from each other. In an example, a separate temporary module can be used, such as by an end user, to accomplish the attachment or detachment. Examples of the temporary module for attaching or detaching the electrostimulation electrode 120 to or from the electrode fixation support member 110 are described below, such as with reference to FIGS. 5A-C.

Under certain circumstances, the electrostimulation electrode 120 may be desired to be detached from the electrode fixation support member 110. For example, a stimulation catheter or lead incorporating the electrostimulation electrode 120 may be replaced or revised. For another example, the untethered electrostimulator device, which can be an embodiment of the electrostimulation electrode 120, can have a depleted or near-depleted battery or other power source, thus prompting a device changeout or device upgrade. To facilitate the detachment, at least some part of the electrostimulation electrode 120, e.g., such as including the second coupler feature 123, can be covered on its surface or otherwise provided with a surface that can include a material that can inhibit tissue ingrowth. An example of such material can include an expanded Polytetrafluoroethylene (ePTFE) coating, such as with pores that can be sized (e.g., <5 μm) such as to allow fluid to pass through, but not tissue and blood cells. Other examples of the tissue ingrowth-inhibition material can include electro-spun polyurethane or micro-textured material. The tissue ingrowth-inhibition material can additionally or alternatively be coated on or otherwise provided at a portion of the electrode fixation support member 110 such as at the first coupler feature 113 or at the surface contacting the electrostimulation electrode 120.

Figure 2A:
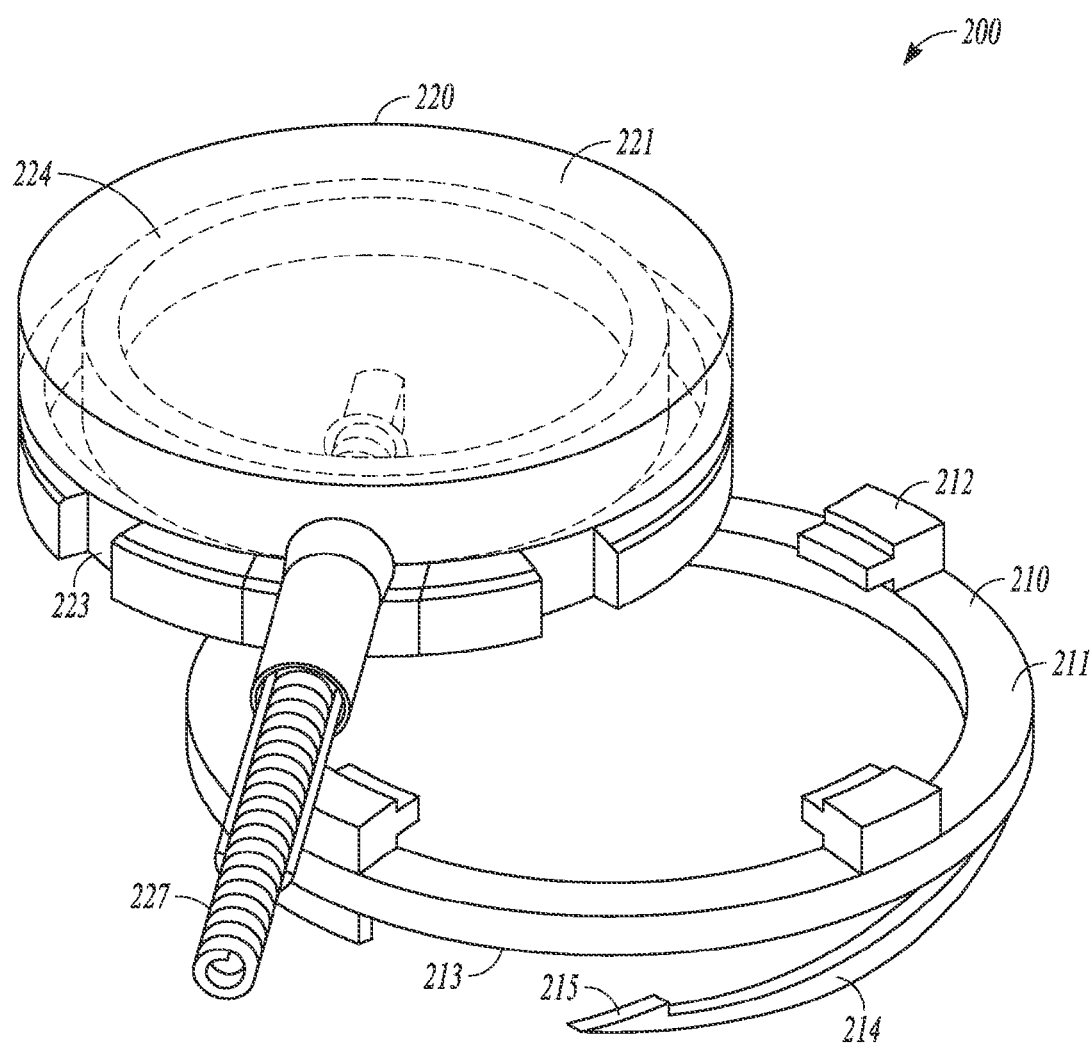
FIGS. 2A-C illustrate examples of a modular heart stimulation system.
Figure 2B:
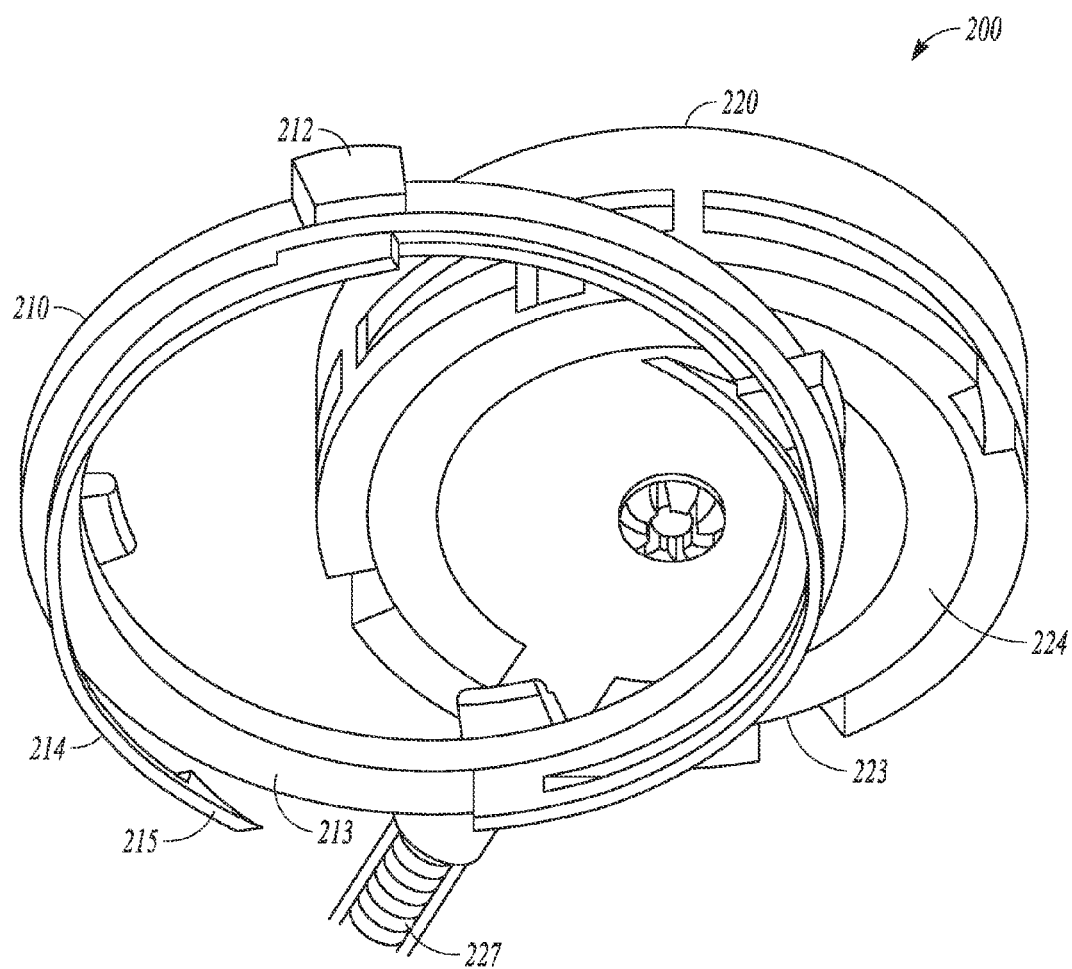
Figure 2C:
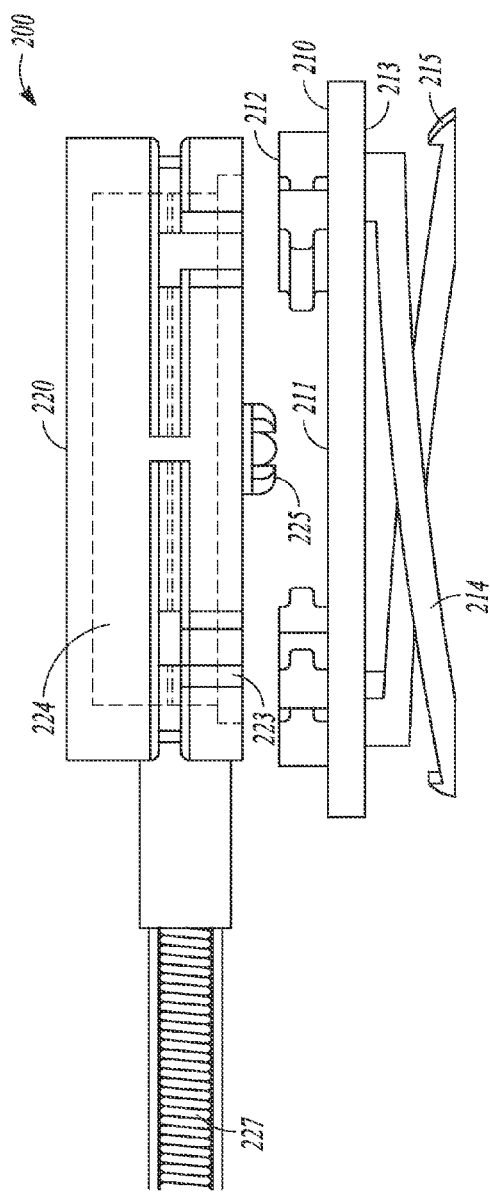

FIGS. 2A-C illustrate examples of a modular heart stimulation system 200, which can be an embodiment of the implantable apparatus 100 that can include the modular electrostimulation electrode assembly 101. FIG. 2A illustrates a top view, FIG. 2B a bottom view, and FIG. 2C a side view of an example of the heart stimulation system 200. In an example, the heart stimulation system 200 can be used to provide temporary or chronic stimulation such as bradycardia pacing, tachycardia pacing, cardioversion or defibrillation shock, or cardiac resynchronization electrostimulation, such as for treating congestive heart failure.

The heart stimulation system 200 can include an electrode fixation support member 210 and an electrostimulation electrode member 220. The fixation support member 210 can be an embodiment of the electrode fixation support member 110, and can include a ring-shaped body which can be configured to lay flat against or otherwise conform to a surface of a heart or other target region of a subject. The ring-shaped body can define a centrally located open portal that can be sized, shaped, or otherwise configured for permitting electrode access to the surface of the heart therethrough. The central open portal can additionally or alternatively provide a viewable zone that can allow the end user to visualize, through the portal, the location where the fixation support member 210 interfaces with the heart surface. Although the fixation support member 210 can have a round shape, such as illustrated in FIGS. 2A-C, another symmetric or asymmetric shape can be used, such as an oval, an ellipse, a square or other polygon, such as can allow the fixation support member 210 to include an open portal, such as for permitting electrode access or an un-obstructed view of the electrode positioning.

The fixation support member 210 can have a top surface 211 and a bottom surface 213. The top surface 211 can include a first coupler feature 212, such as one or a plurality of snap-fit couplers that can be located on the circumference of the ring-shaped fixation support member 210, such as illustrated in FIGS. 2A-C. The first coupler feature 212 can be configured to be physically coupled to a corresponding second coupler feature 223 on the electro-stimulation electrode 220, such as for causing the fixation support member 210 and the electro-stimulation electrode 220 to securely attach to each other. The first coupler feature 211 can also be de-coupled from the second coupler feature 223, such as for causing the fixation support member 210 and the electro-stimulation electrode 220 to detach from each other. One or more other coupling features, such as rotation or screw-in coupling, slide-in engagement, or locking-in coupling can additionally or alternatively be used.

The bottom surface 213 can include an outward extending active fixation member 214. The active fixation member 214 can be sized, shaped, or otherwise configured to be oriented toward and to engage the surface of the heart. As illustrated in FIGS. 2A-C, the active fixation member 214 can include a pair of rotationally-oriented barbs 215 that can be sized, shaped, or otherwise configured to engage the heart, such as when the fixation support member is rotated with respect to the heart. Although two barbs are shown, various number, orientation, shape, or configurations of the barbs are contemplated, such as can be used for fixation. In an example, the one or more active fixation members can additionally or alternatively include one or more of the screw, hook, helix, or other tissue-penetrating mechanisms. In an example, one or more passive fixation members such as one or more tines, one or more fins, one or more helices, or one or more other extension structures can be used either as an alternative to or in conjunction with one or more of the active fixation members. The active fixation member 214 can be located on the bottom surface 213 and oriented in a comparable curvature as the ring-shaped fixation support member 210, such that the active fixation member 214 need not block all or a portion of the viewable zone of the central open portal.

At least a portion of the fixation support member 210 (e.g., including the bottom surface 213 or the active fixation member 214) can be textured or porous, or can be attached to or coated with a porous biomaterial or a porous synthesized material such as to promote tissue ingrowth. The fixation support member can include a suture retention feature. Examples of the suture retention feature on the fixation support member 210 are discussed below, such as with reference to FIG. 3.

The electrostimulation electrode member 220, which is an embodiment of the electrostimulation electrode 120, can include a ring-shaped or disk-shaped body 221, such as can be sized, shaped, or otherwise configured to be comparable to the shape of the fixation support member 210. The circumference of the electrostimulation electrode member 220 can include a second coupler feature 223. The number, shape, size, or configuration of the one or more second coupler features 223 can be compatible with the one or more first coupler features 212, such that the fixation support member 210 and the electrostimulation electrode member 220 can be tightly and securely attached to each other. In an example, the second couple feature 223 can be located on the circumference of the electrostimulation electrode member 220. In an example, the first coupler feature 212 extends to less than half of the height of the electrostimulation electrode member 220 when the fixation support member 210 and the electrostimulation electrode member 220 are attached to each other.

The electrostimulation electrode member 220 can include at least a first electrode 225 and a second electrode 224. When the electrostimulation electrode member 220 is coupled to the electrode fixation support member 210, the first electrode 225 can be located toward the center of the open portal of the electrode fixation support member 210, while the second electrode 224 can be located more laterally from the center of the portal of the electrode fixation support member 210 than the first electrode 225. In an example, such as illustrated in FIG. 2B, the second electrode 224 can include a ring-like electrode that can extend circumferentially about the first electrode 225 and that can be spaced apart from the first electrode 225. The electrodes 224 and 225 can be respectively electrically connected to a stimulator (such as an ambulatory medical device or a PSA circuit) such as via separate conductors that can be mutually insulated and encapsulated in a lead or catheter 227. The electrodes 224 and 225 can be configured to access the target stimulation site on the heart surface as viewable through the central open portal on the electrode fixation support member 210. In an example, such as illustrated in FIG. 2C, one or both of the electrodes 224 and 225 can extend from the bottom surface of the electrostimulation electrode member 220 for a depth longer than the height of the electrode fixation support member 210 affixed to the heart surface, such that the electrodes 224 and 225 can closely contact the heart for stimulation. The lead or catheter 227 can be coupled to the ring-shaped or disk-shaped body 221 such as from a site on the circumference of the electrostimulation electrode member 220.

The stimulator, such as an ambulatory medical device or a PSA circuit, when connected to the electrode assembly carrying at least one of electrodes 224 or 225, can be configured to deliver a unipolar stimulation or a bipolar stimulation. The unipolar stimulation can be provided, such as using one of the first electrode 225 or the second electrode 224, together with a return electrode such as an electrode that can be located on a "can" of an ambulatory medical device. The bi-polar stimulation can be provided, such as where the first electrode 225 can be configured to be a cathode and the second electrode 224 can be configured to be an anode. The ring-like second electrode 224 can be segmented into a plurality of electrodes, such as a plurality of individually addressable electrodes. The first electrode 225 and the plurality of electrodes 224 can form an electrode array, and such as to permit one or multiple stimulation vectors to be configured, such as using pair-wise or other selections of electrodes selected from the electrode array.

Figure 3:
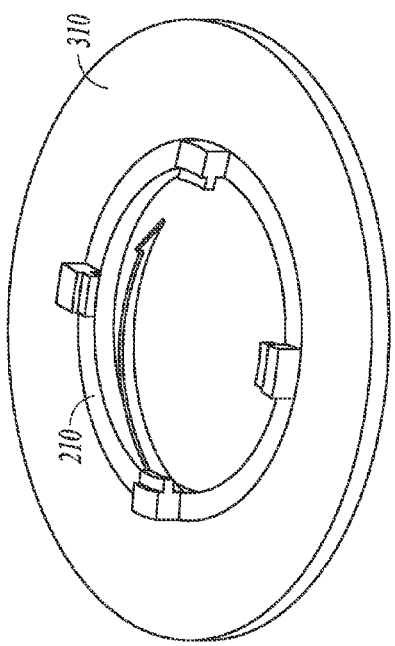
FIG. 3 illustrates an example of a suture retention feature used with an electrode fixation support member.

FIG. 3 illustrates an example of a suture retention feature 310 that can be included in or attached to the electrode fixation support member 210. The suture retention feature 310 can extend circumferentially about at least a portion of the electrode fixation support member 210. In an example, only a portion of the fixation support member 210 can include a sutureable material allowing suturing therethrough such as by passing a needle and suture thread through a penetrable portion of the suture retention feature 310. The suture retention feature 310 can include or consist of a biocompatible material such as a fabric, a polymer, or another biological or synthetic biocompatible material. The suture retention feature can include features including a hole (such as on at least one of the biocompatible material or the electrode fixation support member 210), or a bridge (such as on the electrode fixation support member 210) through which a needle and thread can be passed. The suture retention feature 310 can be coated with, or otherwise include or consist of, material that can be selected for promoting tissue ingrowth, such as porous biological material or porous synthesized material.

Figure 4A:
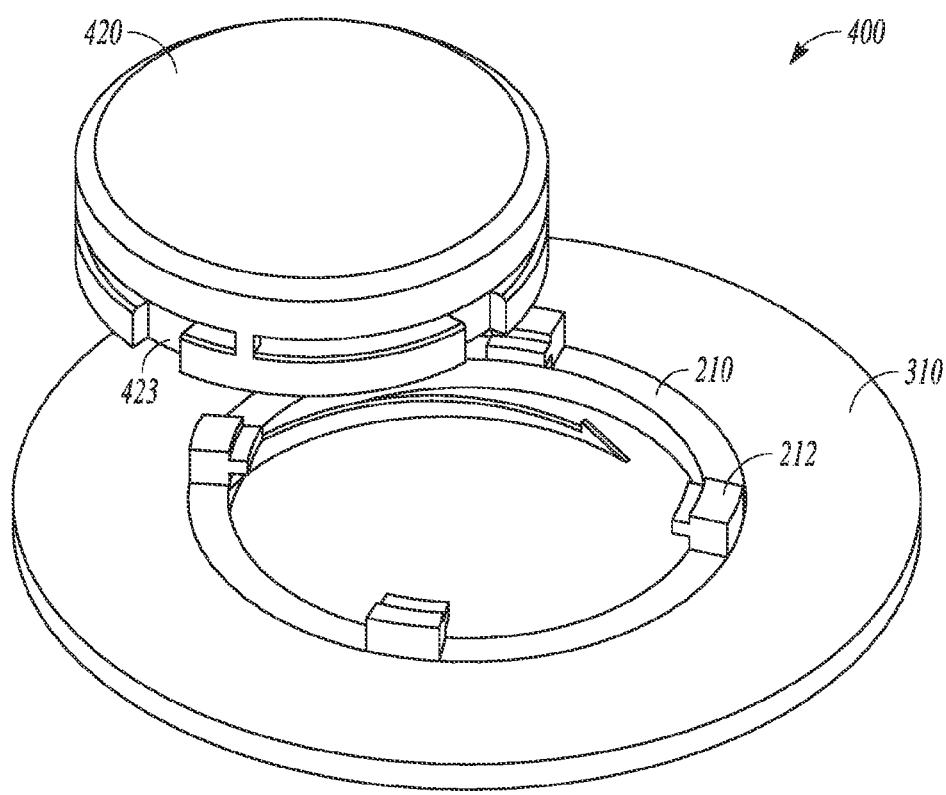
FIGS. 4A-B illustrate examples of a modular heart stimulation system.
Figure 4B:
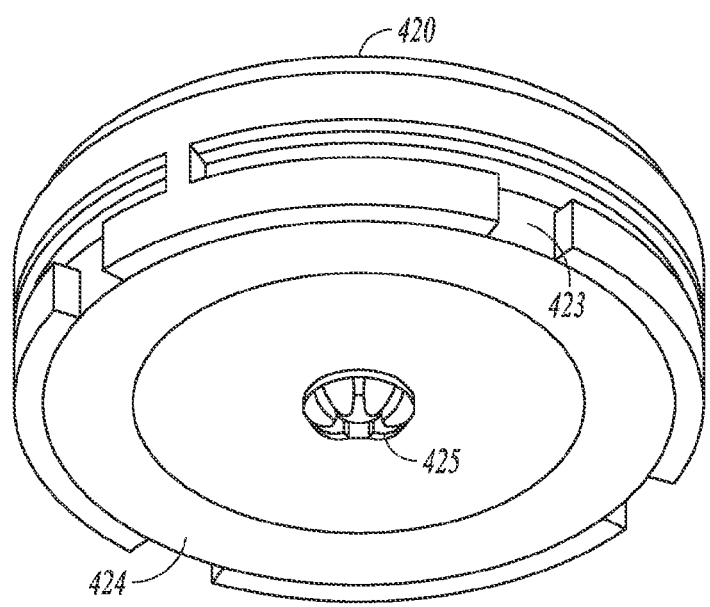

FIGS. 4A-B illustrate examples of a modular heart stimulation system 400, which can be an embodiment of the implantable apparatus 100 that can include the modular electrostimulation electrode assembly 101. The heart stimulation system 400 can include an electrode fixation support member 210 and an untethered electrostimulator device 420 (e.g., a leadless pacemaker). The fixation support member 210, such as described previously in FIGS. 2A-C, can include a ring-shaped body, which can be configured to lay flat against or otherwise conform to the heart surface. The fixation support member 210 can be positioned on the heart surface and can be secured, such as using the rotationally-oriented barbs when the fixation support member 210 is rotated concentrically on a target site of the heart. The fixation support member 210 can also include the suture retention feature 310, such as for permitting the end user to suture therethrough, such as to hold the fixation support member 210 against the heart surface.

The untethered electrostimulator device 420 can be configured to locally generate and locally deliver electrostimulation to the heart or other target site such as to achieve one or more therapeutic effects, such as chronic bradycardia pacing, tachycardia pacing, cardioversion or defibrillation shock, or cardiac resynchronized pacing such as for treating congestive heart failure. The untethered electrostimulator device 420 can include circuitry, instructions (e.g., software or firmware), and a battery or other power source or storage device, or one or more other electrical components or functional modules. The circuitry in the untethered electrostimulator device 420 can be configured to sense and analyze one or more biopotential signals, such as from the heart surface, such as one or more intrinsic electrical signals obtained from the heart using the electrodes, such as before or in response to the electrostimulation to the heart. The housing of the untethered electrostimulator device 420 can be made of one or more biocompatible materials, such as titanium or other material.

The untethered electrostimulator device 420 can have a coupler feature 423 which can be sized, shaped, or otherwise configured to be coupled to the first coupler feature 212 on the fixation support member 210. The coupler feature 423 and the first coupler feature 212 can respectively be sized, shaped, or otherwise configured to be attached securely to each other, such as by an end user, such as to attach the untethered electrostimulator device 420 to the fixation support member 210. The coupler feature 423 and the first coupler feature 212 can also be detached from each other, such as by an end user, such as to detach the untethered electrostimulator device 420 and the fixation support member 210 from each other. Examples of the coupler feature 423 can include one or more of a snap-fit coupling, a rotation or a screwing-in coupling, a slide-in engagement, or one or more other locking mechanisms.

The untethered electrostimulator device 420 can include at least a first electrode 425 and a second electrode 424. As illustrated in FIG. 4B, the first electrode 425 can be configured to be located toward the center of the untethered electrostimulator device 420, and thereby located in the center of the open portal of the electrode fixation support member 210 when the untethered electrostimulator device 420 is attached to the electrode fixation support member 210. The second electrode 424 can be located at a position lateral from the center of the untethered electrostimulator device 420 than the first electrode 425. The second electrode 424 can include a ring-like electrode that can extend circumferentially about the first electrode 425 and that can be spaced apart from the first electrode 425.

The untethered electrostimulator device 420 can be configured to deliver a unipolar stimulation such as using one of the first electrode 425 or the second electrode 424, and using a return electrode such as a housing or "can" of the untethered electrostimulator device 420. A bi-polar stimulation can be provided, such as where the first electrode 425 can be configured to be a cathode and the second electrode 424 can be configured to be an anode. A ring-like second electrode 424 can be segmented into a plurality of electrodes, such as individually addressable electrodes. The first electrode 425 and the plurality of electrodes 424 can form an electrode array, and one or multiple stimulation vectors can be provided, such as by using pair-wise or other selections of electrodes selected from the electrode array.

Figure 5A:
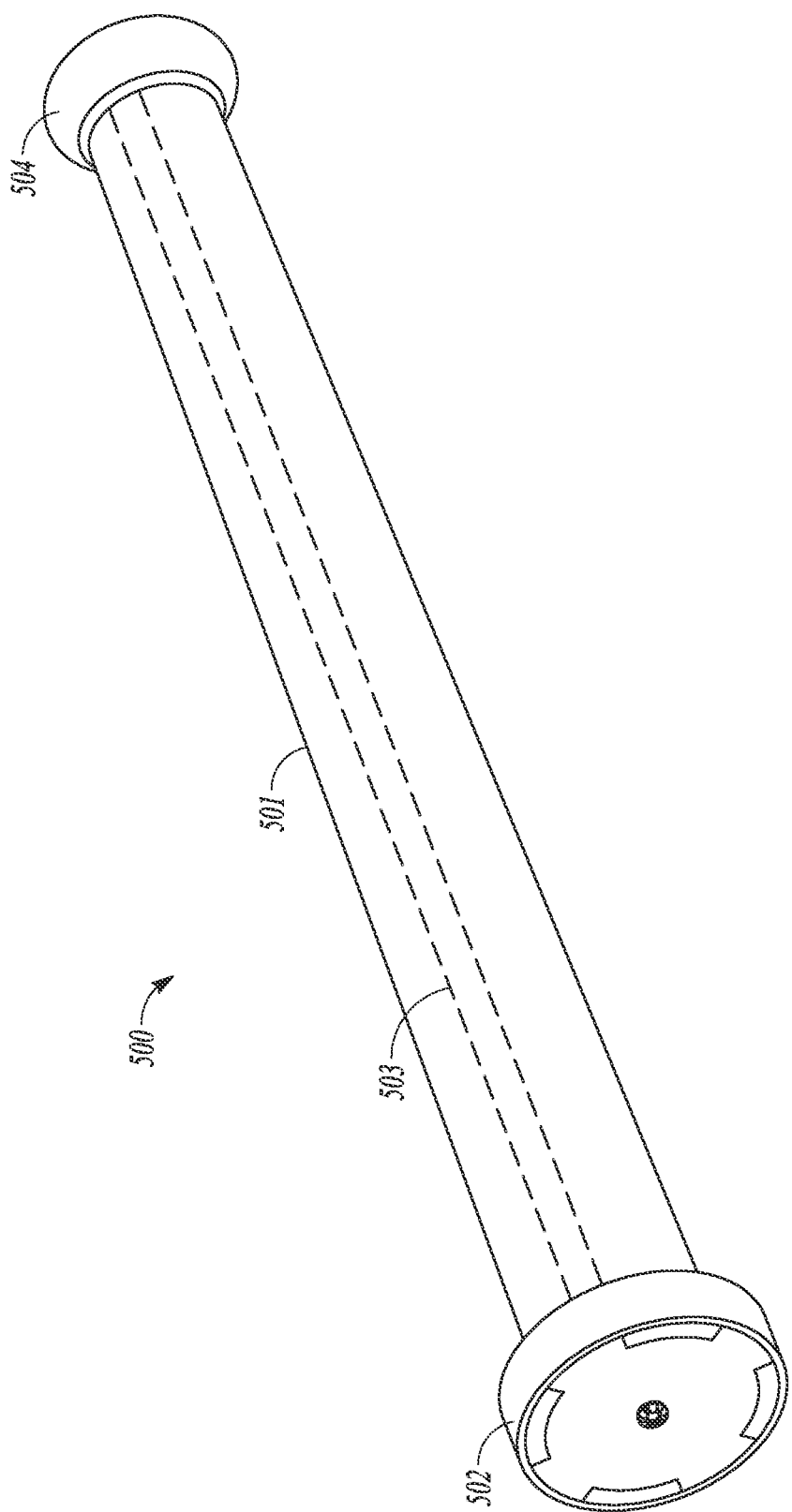
FIGS. 5A-C illustrate examples of a temporary module including a fixation tool.
Figure 5B:
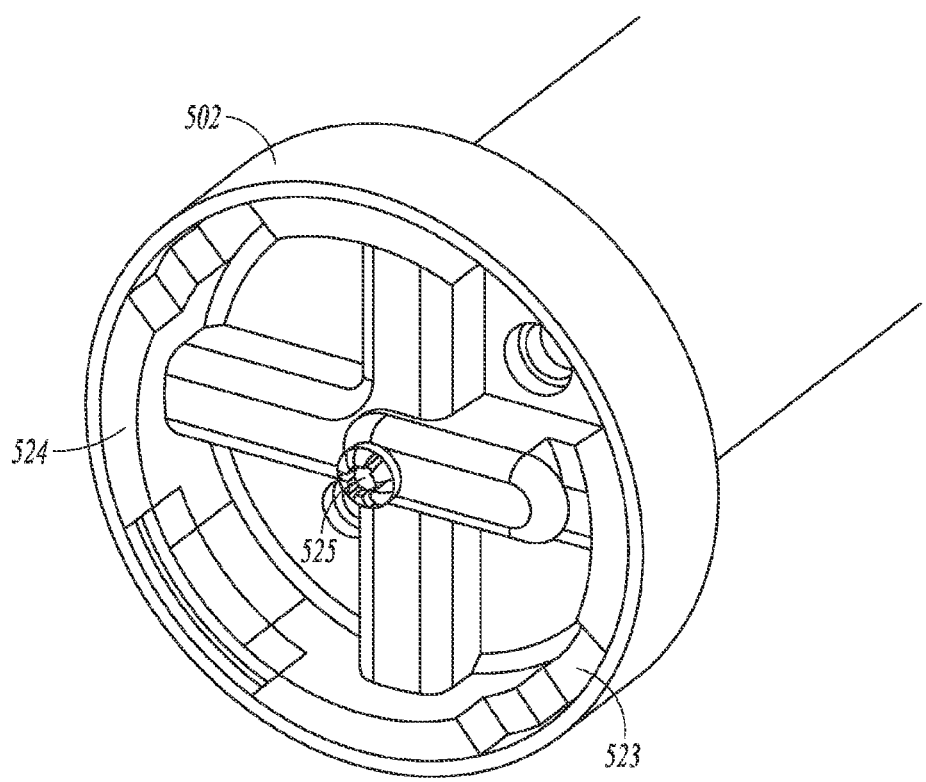
Figure 5C:
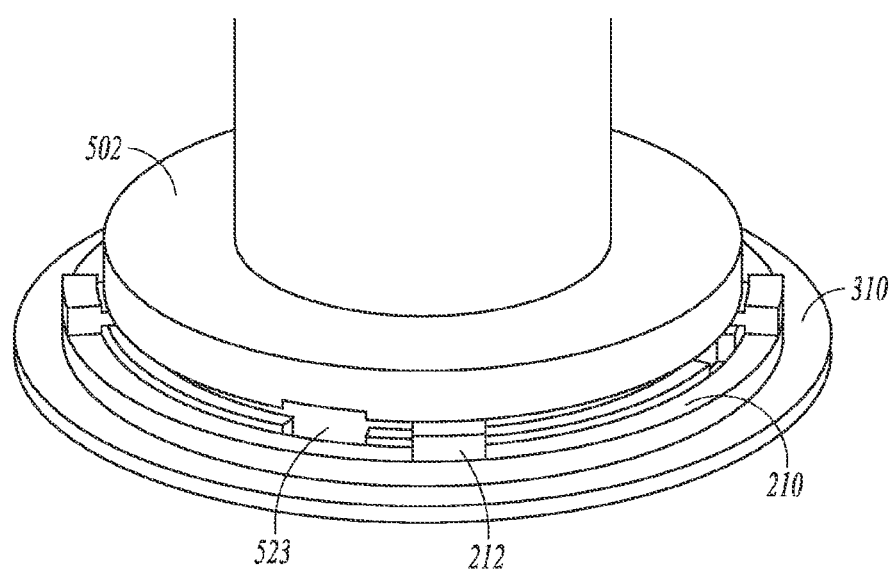

FIGS. 5A-C illustrate examples of a temporary module that can include a fixation tool 500. The fixation tool 500, e.g., when used with the modular heart stimulation system 200 or the modular heart stimulation system 400, can be configured to be used, such as by an end user, to locate a desired location on the heart surface for stimulation, and to affix the fixation support member 210 at the target site of the heart surface. The fixation tool 500 can include a delivery member 501, an engagement member 502, and a cable 503.

The delivery member 501 can have at least a partially elongated body, such as illustrated in FIG. 5A. The delivery member 501 can be shaped, sized, or otherwise configured for approaching the heart surface such as through a sub-xiphoid approach. The delivery member 501, on its distal end (i.e., the end to be oriented toward the heart), can be coupled to the engagement member 502; and on its proximal end 504 (i.e., the end to be oriented away from the heart), can be configured to be connected to a temporary stimulation system. The elongated body of the delivery member 501 can internally house or externally carry the cable 504 that can be configured to conduct electrostimulation toward the heart surface and to conduct the electrical signals sensed from the heart surface.

The engagement member 502 can be coupled to the distal end of the delivery member 501. The engagement member 502 can be an unitary part of the delivery member 501, or can be a portion of the delivery member 501. As illustrated in FIG. 5B, the engagement member 502 can have an open surface on its distal end, which can be shaped, sized, or otherwise configured to contact the heart surface. The engagement member 502 can include a first electrode 525 that can be configured to be located toward the center of the engagement member 502, and a second electrode 524 that can be configured to be located more laterally from the center of the engagement member 502 than the first electrode 525. The second electrode 524 can include a ring-like electrode that can extend circumferentially about the first electrode 425 and that can be spaced apart from the first electrode 425. Additionally or alternatively, such as illustrated in FIG. 5B, the second electrode 524 can include a plurality of electrodes that can be circumferentially located around the first electrode 525. The engagement member 502 can include an electrode array with a specified number, orientation, or spatial distribution of the electrodes, such as a linear array, a planar array, or a three-dimensional array. The electrostimulation electrodes 524 and 525 can individually be electrically connected to a stimulator such as via separate conductors that can be mutually insulated and that can be encapsulated in a cable 503. The stimulator, such as an external pacing system analyzer (PSA) circuit, can be coupled to the delivery member 501, such as at the proximal end 504.

The engagement member can have a third coupler feature 523, which can be sized, shaped, or otherwise configured to be coupled to the first coupler feature 212 on the fixation support member 210. In an example, such as illustrated in FIG. 5C, the third coupler feature 523 and the first coupler feature 212 can individually be sized, shaped, or otherwise configured to be attached securely to each other such as by an end user, such as to attach the engagement member 502 and the fixation support member 210 to each other. The third coupler feature 523 and the first coupler feature 212 can also be configured to be detached from each other, such as by an end user, such as to detach the engagement member 502 and the fixation support member 210 from each other. Examples of the third coupler feature 523 can include one or more of a snap-fit coupling, a rotation or screw-in coupling, a slide-in engagement, or one or more other coupling, engagement, or locking mechanisms.

When the engagement member 502 is attached to the electrode fixation support member 210, the electrostimulation electrodes 524 and 525 can be inserted through the open portal of the fixation support member 210, such as to contact the surface of the heart. Without affixing the fixation support member 210 to the heart surface, the fixation tool 500 can be configured to be used, such as by an end user, (e.g., by holding the elongated delivery member 501) to probe around different locations of the heart surface such as to locate a desired region for anchoring the fixation support member 210. The electrostimulation electrodes 524 and 525 can be configured to deliver the electrostimulation to the heart tissue or to sense one or more biopotential signals from the heart surface. For example, the electrostimulation electrodes 524 and 525 can be configured to sense the heart signals in response to the electrostimulation, and a PSA circuit electrically connected to the fixation tool 500 can be used to analyze the electrical signals such as to determine an electrostimulation threshold value of the electrostimulation electrode at a particular location on the heart. By probing around different locations of the heart tissue, electrostimulation threshold values at various sites on the heart can be determined. When a desired electrostimulation threshold value is obtained, a desirable fixation site can be declared as having been detected. The desirable fixation site can be determined using other electrical, mechanical, or physiological information either as an alternative or in addition to the electrostimulation threshold value. Examples of other information can include ultrasound or other imaging, one or more physiologic signals obtained in response to the electrostimulation delivered through the electrodes 524 and 525, such as can be sensed by one or more physiological sensors within or external to the fixation tool 500.

Upon detecting the desirable fixation site, the fixation tool 500 can be used to affix the electrode fixation support member 210 at the position corresponding to the desired threshold value. Depending on the fixation mechanism on the electrode fixation support member 210, an appropriate maneuver can be used by the end user to achieve the desired fixation. For example, to engage an outward extending active fixation member 214 into the heart surface, the fixation tool 500 can be twisted in the same rotating penetrating direction as the rotationally-oriented barbs 215. Once the electrode fixation support member 210 is securely affixed to the desired location of the heart, the third coupler feature 523 can be detached from the first coupler feature 212, such as by an end user, thereby releasing the engagement member 502 from the fixation support member 210.

The fixation tool 500 can be configured to be used, such as by an end user, such as to attach or detach the electrostimulation electrode member 220 or the untethered electrostimulator device 420 to or from the fixation support member 210. The attachment or detachment can be accomplished by using a tool, such as a dedicated electrostimulation electrode placement tool. The dedicated electrostimulation electrode placement tool can have a size, shape, or other configuration such as can be comparable to the fixation tool 500. Because no probing functionality is needed when attaching the electrostimulation electrode member 220 and the fixation support member 210, the dedicated electrostimulation electrode placement tool can omit the electrostimulation electrodes such as 524 and 525 on the fixation tool 500. The dedicated electrostimulation electrode placement tool can include a coupler feature or other securing feature such as to securely attach to the electrostimulation electrode member 220 or to the untethered electrostimulator device 420, or transport and attach the electrostimulation electrode member 220 or the untethered electrostimulator device 420 to the fixation support member 210. The dedicated electrostimulation electrode placement tool can also be configured to allow it to be used to cause or facilitate the detachment between the electrostimulation electrode member 220 or the untethered electrostimulator device 420 and the fixation support member 210 from each other.

Figure 6:
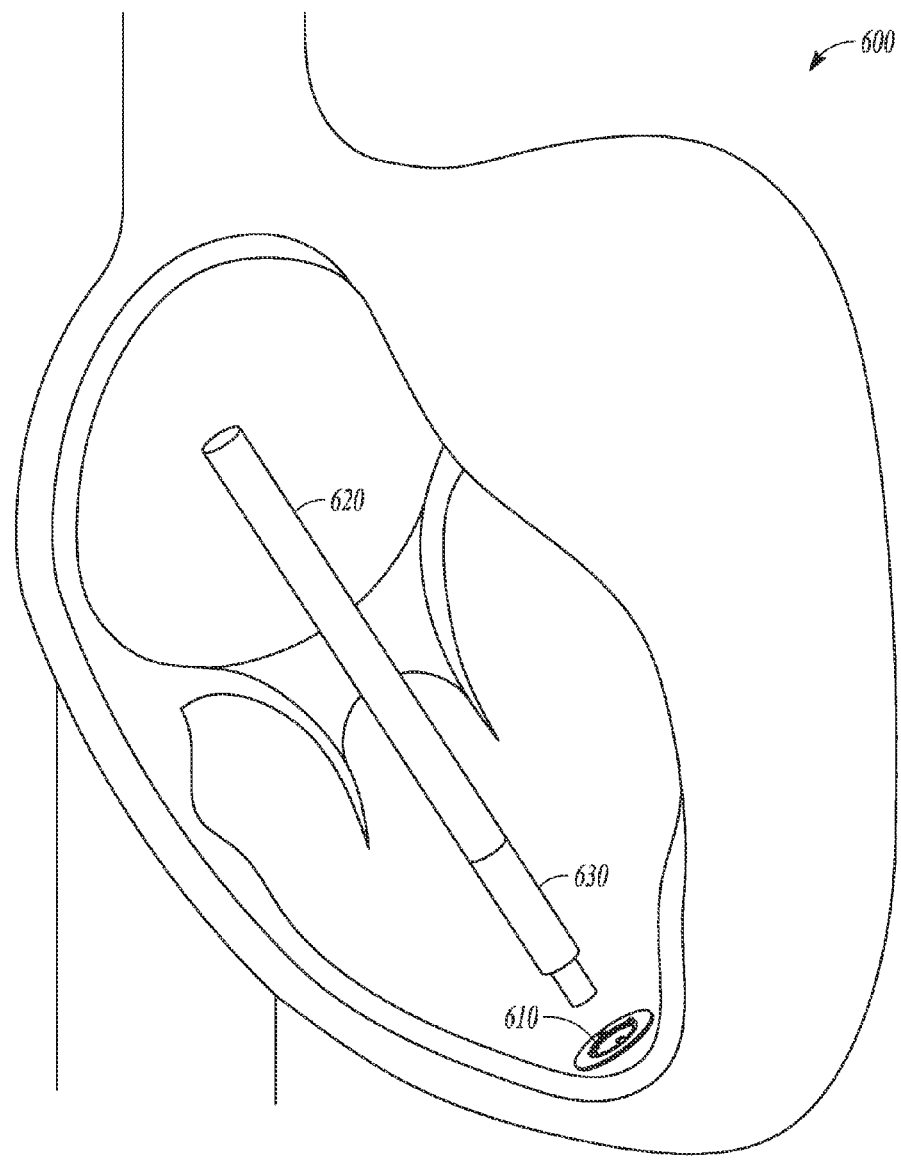
FIG. 6 illustrates an example of a modular endocardial stimulation system and portions of an environment in which the endocardial stimulation system can operate.

FIG. 6 illustrates an example of a modular endocardial stimulation system 600 and portions of an environment in which the endocardial stimulation system 600 can operate. The endocardial stimulation system 600 can be configured to stimulate the heart such as to achieve a desired diagnostic or therapeutic effect such as chronic bradycardia pacing, tachycardia pacing, cardioversion or defibrillation shock, or cardiac resynchronized pacing such as for treating congestive heart failure. The endocardial stimulation system 600 can include a fixation base 610, an insertion tool 620, and pacing seed 630.

The fixation base 610 and the pacing seed 630 can be a part of a modular stimulation system such as can be comparable to the modular heart stimulation system 200 such as discussed in FIGS. 2A-C, or a modular heart stimulation system 400 such as discussed in FIGS. 4A-B. For example, the fixation base 610 can have a size, shape, or configuration that can be comparable to the electrode fixation support member 210. The ring-shaped fixation base 610 can be affixed to a desired location inside a heart chamber (e.g., at an apical or other region in the right ventricle, such as illustrated in FIG. 6) or in a blood vessel inside or on the heart (e.g., a pulmonary artery or a coronary vein). The fixation base 610 can include at least one of an active fixation feature, a passive fixation feature, a suture retention feature, a porous or textured finish, or a porous or textured material covered on at least a portion of the fixation base 610 such as can be configured to promote tissue ingrowth.

The insertion tool 620 can be configured to be used, such as by an end user, such as to affix the fixation base 610 to the target endocardial site, and to attach or detach the pacing seed 630 to or from the fixation base 610. The fixation base 610 can have a size, shape, or configuration that can be comparable to the fixation tool 500 or to the dedicated electrostimulation electrode placement tool, such as discussed with respect to FIGS. 5A-C. The insertion tool 620 and the fixation base 610 can be attached to or detached from each other, such as through respective one or more coupler features.

The pacing seed 630 can include one or more electrostimulation electrodes that can be configured for endocardial electrostimulation. The pacing seed 630 can have a configuration that can be comparable to the electrostimulation electrode member 220. In an example, such as illustrated in FIG. 6, the pacing seed 630 can have a configuration that can be comparable to the untethered electrostimulator device 420. The pacing seed 630 and the insertion tool 620 can be attached to or detached from each other such as using respective one or more coupler features.

The fixation base 610 and the pacing seed 630 can both be attached to the insertion tool 620 before the insertion tool 620 is inserted into the heart. The fixation base 610 can be attached on or along the insertion tool 620 such as at a position distal to the pacing seed (such as the distal end of the insertion tool 620). Like the fixation tool 500, the insertion tool 620 can include electrostimulation electrodes that can be configured to deliver the electrical stimulation and sense the evoked heart signal response such as to determine the electrostimulation threshold. Once a desired stimulation site has been found, such as after probing around the endocardial region, the insertion tool 620 can be maneuvered by an end user such as to position and affix the fixation base 610 to the desired stimulation site. The pacing seed 630 and the insertion tool 620 can then be detached from each other, and the pacing seed 630 can be attached to the fixation base 610.

In an example, the pacing seed 630 and the fixation base 610 can be attached to each other before inserting the insertion tool into the heart. After finding the desired stimulation site, the fixation base 610 can be affixed to the heart tissue, and the fixation base 610 and the pacing seed 630 can then be jointly detached from the insertion tool 620. If the pacing seed 630 needs to be extracted (e.g., such as for replacement of the pacing seed 630), the insertion tool 620, or a tool comparable to the dedicated electrostimulation electrode placement tool, such as discussed in FIGS. 5A-C, can be used to engage the proximal end (e.g., not contacting the fixation base 610) of the pacing seed 630 such as using the respective coupler features. The insertion tool 620 can then disengage and remove the pacing seed 630 from the fixation base 610, such as leaving the fixation base 610 unaltered in place.

Figure 7:
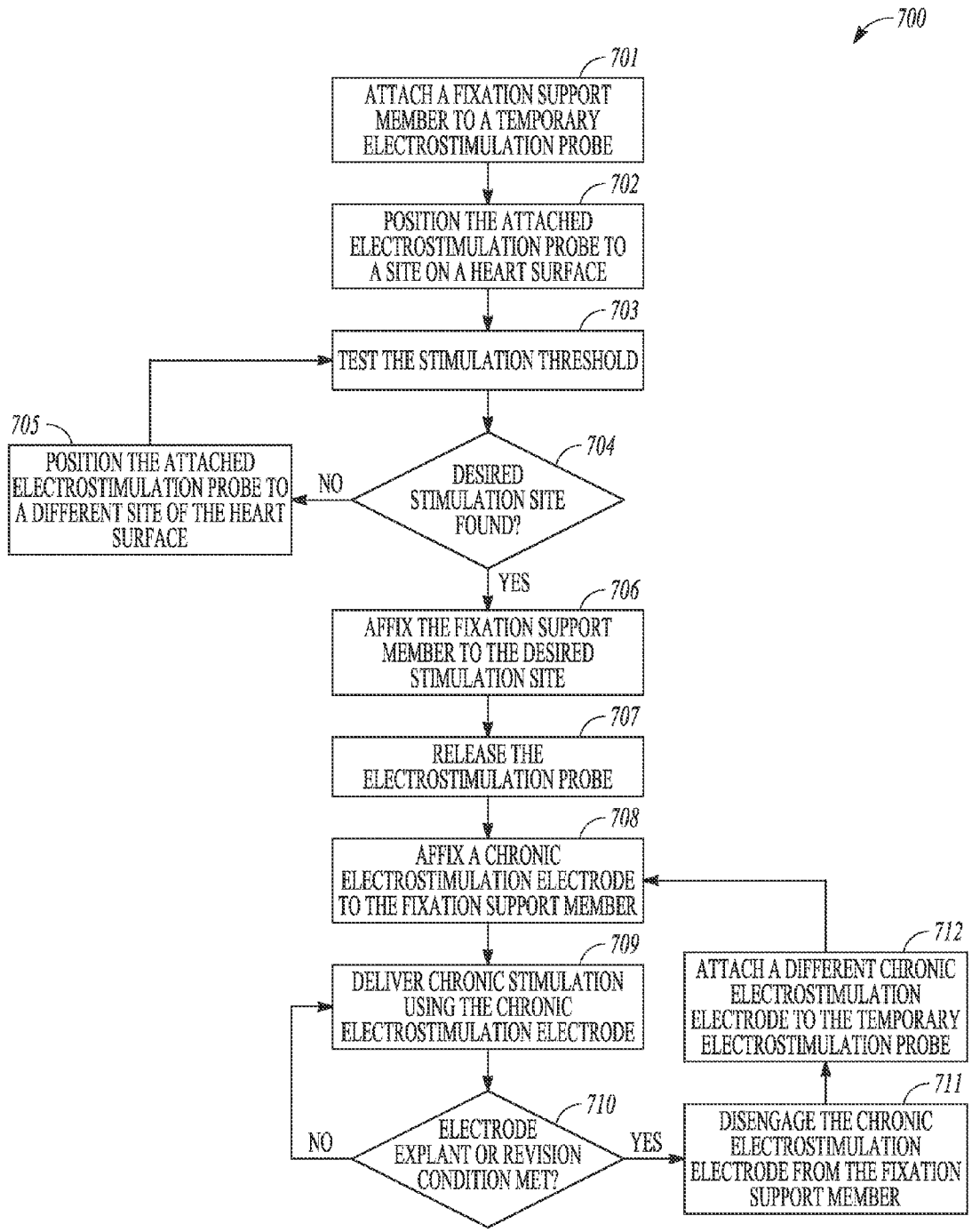
FIG. 7 illustrates an example of a method for stimulating a region of a heart.

FIG. 7 illustrates an example of a method for stimulating a region of a heart, such as using one or more of the modular heart stimulation system 200, the modular heart stimulation system 400, or the modular endocardial stimulation system 600.

At 701, a first module that can include a fixation support member, such as the electrode fixation support member 210, can be attached to a temporary electrostimulation probe. The fixation support member and the temporary electrostimulation probe each can have one or more coupler features that can be sized, shaped, or otherwise configured to snap-fit together, rotated and fit together, slide in, or through one or more other coupling mechanisms. The electrostimulation probe, such as the fixation tool 500 or the inserting tool 620, can have one or more electrodes such as located at the distal end of the electrostimulation probe. The electrodes can be individually addressed and connected to a stimulation system such as an external pacing system analyzer (PSA) circuit that can generate and transmit the electrostimulation toward the electrodes such as using a cable, a catheter, or a lead.

At 702, the temporary electrostimulation probe can be advanced to a target stimulation site such as an epicardial region or an endocardial region, and can be used to position the attached electrostimulation probe at the target stimulation site. At 703, the electrodes on the temporary electrostimulation probe can be used to transmit electrostimulation pulses from an adjunct stimulator, such as the PSA, to the heart tissue and to sense the resulting biopotential signals from the heart tissue, such as for determining a capture threshold. The electrostimulation pulses can be specified by programming the PSA with one or more stimulation parameters, such as the stimulation pulse amplitude, pulse width, pulse frequency, duty cycle, or pulse waveform, or others. The PSA can analyze the sensed biopotential signal such as to determine the stimulation threshold at the target stimulation site.

At 704, the tested electrostimulation threshold at the target stimulation site can then be compared to at least one specified criterion. In an example, the tested electrostimulation threshold can be compared to a threshold value or to a range of desired stimulation thresholds. If the specified criterion is not met, then at 705 the temporary electrostimulation probe can be moved by the end user to a different target stimulation site, such as near the previous stimulation site on the heart surface. At 703, the stimulation threshold can then be tested for the newly positioned site. The desired stimulation site can be determined using information other than, or in addition to, the stimulation threshold determined at 703. For example, a physiologic sensor can be used to sense a physiologic signal, such as in response to the electrostimulation delivered through the electrodes on the temporary electrostimulation probe. Then, at 704, the desired stimulation site can be determined such as by comparing the sensed physiologic signal to at least one specified criterion. Examples of the one or more physiologic signals that can be used for detecting the desired stimulation response can include one or more of electrocardiograph, electrogram, impedance sensed at a heart region, heart sounds, pressures, contractility, myocardial stress, or the relative timing between two or more sensor signals such as the Q wave to S1 or S2 heart sound interval.

At 704, if the specified at least one criterion is met, the desired stimulation site can be deemed to have been detected. At 706, the temporary electrostimulation probe can be maneuvered to affix the fixation support member to the desired stimulation site such as by using at least one of the fixation mechanisms that can be included in the fixation support member, such as an active fixation feature, a passive fixation feature, a suture retention feature (e.g., for suturing the fixation support member at the desired stimulation site), or a porous finish or porous coating that can be provided on at least a portion of the fixation base 610, such as to promote tissue ingrowth. In an example, using an active fixation device can include rotating the fixation support member such as to engage a rotationally-oriented barb with the heart tissue.

At 707, once the fixation support member is securely and chronically affixed to the desired stimulation site, the temporary electrostimulation probe can be released. A chronic electrostimulation electrode can then be attached to the temporary electrostimulation probe. The chronic electrostimulation electrode can have a coupler feature that can enable the end user to attach the chronic electrostimulation electrode to the temporary electrostimulation probe. At 708, the temporary electrostimulation probe can then be used to position the attached chronic electrostimulation electrode to the location where the fixation support member is affixed, and to attach the chronic electrostimulation electrode to the fixation support member. Examples of using the attachment mechanism can include snap-fitting the chronic electrostimulation electrode to the fixation support member, or rotationally slidably engaging the chronic electrostimulation electrode to the fixation support member. The temporary electrostimulation probe can then be released.

The chronic electrostimulation electrode can be attached to the temporary electrostimulation probe when the fixation support member is attached to the temporary electrostimulation probe at 701. The fixation support member can be attached on or along the temporary electrostimulation probe such as at a position that can be distal to the chronic electrostimulation electrode. At 706, once the fixation support member is affixed to the desired stimulation site, the fixation support member and the attached chronic electrostimulation electrode can both be released from the electrostimulation probe. The fixation support member and the chronic electrostimulation electrode can remain securely attached to each other at the desired stimulation site.

At 709, the chronic electrostimulation electrode can deliver chronic stimulation to the target stimulation site. The chronic electrostimulation electrode, such as the electrostimulation electrode member 220, can include or can be coupled to an ambulatory medical device that can generate the chronic stimulation. The chronic electrostimulation electrode can be a part of an untethered electrostimulator device 420 that can locally generate and locally deliver the chronic stimulation.

The method 700 can include optional steps, such as in performing the heart stimulation when the chronic electrostimulation electrode is desired to be explanted or removed. These additional steps can be performed together with or separately from the method 700.

Conditions for chronic electrostimulation electrode removal may include, for example, chronic electrostimulation electrode malfunction, fracture or upgrade of a lead or cable connecting the chronic electrostimulation electrode to a separately located ambulatory medical device, battery or other power source depletion of the untethered electrostimulator device attached to the fixation support member, or device changeout or device upgrade. At 709, if no explant or revision is needed, then the electrostimulation can remain. At 710, if one or more of these conditions are met, then at 711 the chronic electrostimulation electrode can be detached from the fixation support member, such as by using the temporary electrostimulation probe. At 712, a different chronic electrostimulation electrode can be attached to the temporary electrostimulation probe. Following a similar method as in 708, the different chronic electrostimulation electrode can be attached to the fixation support member such as to provide desired electrostimulation.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An implantable apparatus comprising:
a modular electrostimulation electrode assembly including:
a first module, including a fixation support member that is configured to fix the first module to a surface of a heart of a subject, the fixation support member defining a centrally located open portal that is configured for permitting electrode access to the surface of the heart therethrough, wherein the first module includes a first coupler feature;
a second module, including an electrostimulation electrode that is configured to contact the surface of the heart through the centrally located open portal of the fixation support member when the first module is coupled to the second module, wherein the second module includes a second coupler feature;
wherein the first and second coupler features are configured to be end user-attached securely to each other and end user-detached from each other to respectively attach the first and second modules to each other and detach the first and second modules from each other; and
wherein the second module is configured to remain attached to the first module via the first and second coupler features to provide electro-stimulation to the heart of the subject, and/or sense cardiac signals, via the electrostimulation electrode until such time as the end user detaches the second module from the first module and removes the second module from the heart of the subject while leaving the first module attached to the heart via the fixation support member of the first module.

2. The apparatus of claim 1, wherein the second module includes a housing that includes at least one of an electrostimulation generation circuit or a cardiac signal sensing circuit.

3. The apparatus of claim 1, wherein the fixation support member defines a ring that defines the centrally located open portal that is configured for permitting electrode access to the surface of the heart therethrough.

4. The apparatus of claim 1, wherein the fixation support member includes an outward extending active fixation member that is configured to be oriented toward and to engage the surface of the heart.

5. The apparatus of claim 4, wherein the active fixation member includes a pair of rotationally-oriented barbs that are configured to engage the heart when the fixation support member is rotated with respect to the heart.

6. The apparatus of claim 1, wherein the fixation support member includes a suture retention feature.

7. The apparatus of claim 1, wherein the first and second coupler features are configured to snap-fit together.

8. The apparatus of claim 1, wherein the first and second coupler features are configured to rotate or otherwise slide into engagement with each other.

9. The apparatus of claim 1, wherein at least a portion of the fixation support member is textured or porous to promote tissue ingrowth.

10. The apparatus of claim 1, wherein at least a portion of the fixation support member includes a fabric configured to permit at least one of suturing therethrough or tissue ingrowth therein.

11. The apparatus of claim 1, further comprising a cable, configured to be connected to the second module and to a separate implantable apparatus.

12. The apparatus of claim 1, further comprising a temporary third module, including:
an electrostimulation electrode that is configured to be inserted through the portal of the fixation support member to contact the surface of the heart;
a third coupler feature that is configured to permit the third module to be temporarily end user-attached to the first module and end user-detached from the first module;
a cable extending outward from at least a portion of the third module, the cable configured to be connectable to an external pacing system analyzer (PSA) circuit to determine an electrostimulation threshold value of the electrostimulation electrode at a particular location on the heart; and
an at least partially elongated delivery member, configured to allow the third module to be temporarily end user-attached to the first module and end user-detached from the first module such that the electrostimulation electrode of the third module is insertable through the portal of the fixation support member to contact the surface of the heart, and to allow the fixation support member to be secured to a surface of the heart at a desired location.

13. The apparatus of claim 1, wherein the second module includes:
the electrostimulation electrode, configured to be located toward the center of the portal of the fixation support member of the first module when the second module is coupled to the first module; and
a second electrode, located more laterally from the center of the portal of the fixation support member than the electrostimulation electrode when the second module is coupled to the first module.

14. The apparatus of claim 13, wherein the second electrode includes a ring-like electrode extending circumferentially about the electrostimulation electrode and spaced apart from the electrostimulation electrode.

15. The apparatus of claim 14, wherein the ring-like second electrode is segmented into a plurality of individually addressable electrodes.

* * * * *